United States Patent
Needham et al.

(10) Patent No.: US 6,261,582 B1
(45) Date of Patent: Jul. 17, 2001

(54) SURGICAL METHOD AND COMPOSITION THEREFOR

(75) Inventors: Charles W. Needham, Norwalk, CT (US); R. John Hurlbert, Alberta (CA); Nicholas Theodore; Volker K. H. Sonntag, both of Phoenix, AZ (US)

(73) Assignee: C. R. Bard, Inc., Murray Hill, NJ (US)

( * ) Notice: Subject to any disclaimer, the term of this patent is extended or adjusted under 35 U.S.C. 154(b) by 0 days.

(21) Appl. No.: 09/077,340

(22) PCT Filed: Oct. 14, 1997

(86) PCT No.: PCT/US97/18756
 § 371 Date: May 27, 1998
 § 102(e) Date: May 27, 1998

(87) PCT Pub. No.: WO98/16197
 PCT Pub. Date: Apr. 23, 1998

(30) Foreign Application Priority Data

Oct. 15, 1996 (US) .................................................. 60/028489
Oct. 14, 1997 (US) ..................................... PCT/US97/18756

(51) Int. Cl.[7] ........................... A61K 38/00; A01N 25/26
(52) U.S. Cl. ........................ 424/419; 424/423; 424/426; 514/12
(58) Field of Search ..................................... 424/419, 426, 424/423; 514/12

(56) References Cited

U.S. PATENT DOCUMENTS

| | | | | |
|---|---|---|---|---|
| 4,016,877 | * | 4/1977 | Cruz et al. ............................ | 128/156 |
| 5,124,155 | * | 6/1992 | Reich .................................... | 424/428 |
| 5,227,165 | * | 7/1993 | Domb et al. ......................... | 424/450 |
| 5,458,631 | * | 10/1995 | Xavier .................................. | 424/450 |
| 5,919,473 | * | 6/1999 | Elkhoury .............................. | 424/422 |
| 5,922,340 | * | 7/1999 | Berde et al. .......................... | 424/426 |

OTHER PUBLICATIONS

Needham et al, Conn. Med., vol. 60, # 3, pp. 141–143 (abstract), 1996.*

* cited by examiner

*Primary Examiner*—James H. Reamer
(74) *Attorney, Agent, or Firm*—Pitney, Hardin, Kipp & Szuch, LLP (57) ABSTRACT

Administration of a morphine-based analgesic paste directly to the epidural space during lumbar decompressive surgery significantly improves post-operative pain control, reduces prescribed analgesic consumption, and improves overall health perception for a period of up to 6 weeks following surgery. In a series of 60 patients no treatment related complications attributable to the paste were observed. This post-operative pain control strategy may provide a new gold-standard of care patients undergoing lumbar disectomy or laminectomy.

12 Claims, 5 Drawing Sheets

SURGICAL METHOD AND COMPOSITION THEREFOR

This application claims priority of Provisional U.S. Application No. 60/028,489 filed Oct. 15, 1996.

BACKGROUND OF THE INVENTION

1. Field of the Invention

This invention relates to a surgical method and analgesic compositions for use in surgery. A composition of the present invention is applied during surgery to reduce pain.

2. Brief Description of Related Art

Following surgery, all patients experience some degree of discomfort associated with tissue dissection and removal of tissue during the surgery, at the operative site. Precise mechanisms involved in the production of pain are not fully understood. Pain management is largely composed of systemic administration of narcotics, either orally or parenterally, in the acute and convalescing postoperative state. Systemic administration can be accompanied by side effects, including nausea, vomiting, headache, dizziness, mental disturbance, sedation, constipation, respiratory depression and hypotension. Patient discomfort from pain and side effects of medication can impede patient mobilization, result in longer hospital stays and delay a person's return to normal activities such as employment.

In lumbar surgery, for example, pain arises from the skin incision, dissection and retraction of paraspinal musculature, removal of bony and ligamentous structures, and from direct trauma to the neural elements. Although the relative contribution of each of these is unknown, and might well vary, it is known that local measures such as local anaesthetic infiltration or epidural block, directed towards all of the mentioned structures can reduce postoperative pain.

Epidural administration of analgesics is a known method of pain control in various types of surgery: childbirth [Tan et al., 1994; Keller et al., 1995; Lowson et al., 1995]; major abdominal surgery (Dahl et al., 1992; Scott et al., 1995]; aortic repair [Slade, 1994]; thoracotomy [Lubenow et al., 1994; Bouchard et al. 1995; Thomson et al., 1995]; total knee and hip replacement [McBeath et al., 1995]; phantom pain [Miles, 1995]; and for palliation in patients with terminal cancer [Hicks et al., 1994].

A recent review states that since the first use of epidural opioids in 1979, there have been very few studies that properly compare epidural morphine with other administrative routes for the relief of postoperative pain [Cheam et al., 1994].

In a double-blind study, morphine (3 mg) alone, morphine (3 mg) and epinephrine, and saline (3 ml), respectively, were administered to three groups of patients undergoing lumbar laminectomy [Rechtine et al, 1984]. Medication was delivered into the epidural space as a single dose by catheter at completion of the laminectomy. Patients who received morphine went an average of 17 hours before requiring supplemental analgesics in comparison to those of the control (saline) group, who required supplemental analgesics after an average of seven hours. McGill Pain Scale scores, 24 hours after surgery, were also higher in control patients.

In another double-blind study, morphine (3 mg) and saline, respectively, were administered to two groups of patients undergoing laminectomy for disc herniation [Waikakul et al., 1992]. Medications were delivered as a single dose at completion of the surgical procedure. Patients who received morphine had a pain-free postoperative period averaging 6.3 hours compared to those of the control (saline) group, who had a pain-free postoperative period averaging 2.4 hours.

Morphine has been used in combination with methylprednisolone [McNeill et al., 1995]. In a randomized single-blind study, epidural administration of morphine (5 mg) and methylprednisolone (40 mg) significantly reduced the need for analgesia after decompression for spinal stenosis, but not after decompression for herniated disc. A single dose of medication was delivered to the epidural space through a catheter, which was removed at the completion of the surgical procedure.

Epidural administration of a combination of morphine (2 to 4 mg) and methylprednisolone (40 to 80 mg) has also been found to reduce the need for analgesia after lumbar decompressive surgery. Gelatin sponges were impregnated with the medications and the sponges were placed over the exposed dura in a laminotomy defect. The length of hospital stay was found to be less than historical controls. Earlier ambulation and reduced postoperative narcotic use was found for the study group.

The patent literature indicates an ongoing need in the area of operative and post-operative pain relief. For example, U.S. Pat. No. 5,458,631 (Xavier, Oct. 17, 1995) describes a pain relief method using an implantable catheter which includes four circumferential ring electrodes connected to terminals by fine wires embedded in the side wall of the catheter for attachment to a conventional electric pulse generator. A hollow body includes a lumen with a injection portal for continuously administering a pain-relieving agent in a liquid form. Japanese Patent Publication No. 6239746 (Okada, Aug. 30, 1994) apparently describes controlled-release coated morphine microcapsules for infusion into the subarachnoid space or epidural space. U.S. Pat. No. 5,227,165 (Domb et al., Jul. 13, 1993) describes liposheres having an anaesthetic core and phospholipid coat for controlled, extended delivery of a pain relief agent. U.S. Pat. No. 5,124,155 (Reich, Jun. 23, 1992) describes a water swellable wound-healing dressing made up of fibronectin (or analogue thereof) in which can be dispersed various agents, including an analgesic, for delivery. The dressing can include collagens and other proteins. Russian Patent Publication No. 1477390 (Turko et al., May 7, 1989) apparently describes a treatment of osteochondrosis by removal of affect pulp from the disc and filling the cavity with a collagen sponge.

SUMMARY OF THE INVENTION

In one aspect, the present invention provides a medicinal paste for use in a surgical procedure. The paste includes an analgesic and a microfibrillar collagen.

The paste can be used to provide pain relief, for example during an operation, or postoperatively, to a subject for a few hours to a few weeks, typically between about three and six weeks or even longer. Optionally, pain relief is provided from about 1 hour to ten weeks, 1 day to six weeks, 3 days to six weeks, one week to six weeks, two weeks to six weeks or three weeks to six weeks.

The composition can include an analgesic such as morphine, fentanyl, or demerol, or a combination thereof, subject to compatibility requirements. The analgesic may simply be morphine, fentanyl, or demerol. In a preferred embodiment, the analgesic is morphine.

A paste of the present invention can also include an anti-inflammatory agent. The anti-inflammatory agent can be a steroidal compound. The anti-inflammatory agent can be a non-steroidal compound. The anti-inflammatory agent can be a combination of a steroidal and non-steroidal compound, subject to compatibility requirements.

In a preferred embodiment, the anti-inflammatory agent is steroidal and it is methylprednisolone acetate.

A paste of the present invention can include amino caproic acid.

In a preferred embodiment, the invention is a medicinal composition for use in a surgical procedure as an analgesic agent in which the composition is a paste that includes morphine and microfibrillar collagen. The composition can further include methylprednisolone acetate and/or amino caproic acid.

The microfibrillar collagen of a given paste might be in the range of about 100 to about 1000 mg; 200 to 900 mg; 300 to 800 mg; 400 to 650 mg; or 450 to 550 mg. The paste of a preferred embodiment includes 500 mg of microfibrillar collagen. The analgesic might be present in an amount of between about 10 and about 500 mg; or 20 and 400 mg; or 30 and 350 mg; or 40 and 300 mg; or 50 and 250 mg; or 60 and 200 mg; or between 70 and 150 mg. The paste of a preferred embodiment includes 80 mg of morphine. The amino caproic acid of the present invention might be present in an amount of between about loo and 1000 mg; 200 to 900 mg; 300 to 800 mg; 400 to 650 mg; or 450 to 550 mg. The paste of a preferred embodiment includes 500 mg of amino caproic acid. The anti-inflammatory agent of the present invention might be present in an amount of between about 0.1 and about 10 mg; 0.5 and about 5 mg; 0.5 and about 2.5 mg or 0.75 and 1.5 mg. The paste of a preferred embodiment includes 1 mg of methylprednisolone acetate-lidocaine HCl. It will be understood that these are relative amounts and a person skilled in the art can scale these up or down. It will also be understood that if the desired consistency is not obtainable simply by mixing desired amounts of active ingredients, that a suitable amount of an innocuous liquid (for example an isotonic salt solution) could be used to adjust the consistency of the paste. Additional microfibrillar collagen can be used to increase viscosity.

In another aspect, the present invention is a method of treating a mammal. The method includes performing a surgical operation on the mammal that includes an incision which exposes nerves and applying an effective amount of an analgesic paste of the invention to at least some of the exposed nerves so as to provide pain relief to the mammal.

The method of treatment can include the step of closing the incision so as to secure the paste in place to provide prolonged analgesic relief.

The method of treatment can be a surgical operation such as a discectomy or a laminectomy. The discectomy or the laminectomy can be in the lumbar region of the spine, as is the discectomy of a preferred embodiment.

The subject can be a human.

The method can be a treatment for intractable sciatica due to ruptured discs. It can also be a treatment for lumbar stenosis.

A surgical method of the present invention can include making an incision that creates an opening in the lumbodorsal fascia, applying the paste to exposed dura, closing the lumbodorsal fascia and optionally injecting additional analgesic therethrough into the area of the paste. The additional analgesic may also be mixed into the paste of the invention. The invention includes a method of treating a human subject which includes performing a surgical operation on the subject that includes an incision which exposes nerves, preparing a paste comprising a microfibrillar collagen and an analgesic or an anesthetic and applying an effective amount of the paste to at least some of the exposed nerves so as to provide pain relief to the mammal, wherein preparing the paste includes mixing paste components in proportion to each other so as to obtain a consistency sufficient to permit flow of the paste to the at least some of the exposed nerves.

Preparing the paste can further include mixing paste components in proportion to each other so as to also resist migration of the paste from the treated area.

Further, the preparation step can include including sufficient analgesic to provide pain relief to the subject for a period of between about 1 hour to ten weeks, 1 day to six weeks, 3 days to six weeks, one week to six weeks, two weeks to six weeks, or three weeks to six weeks.

According to another aspect, a paste of the invention has a viscosity slightly less than that of toothpaste.

In another aspect the invention includes a dispenser in combination with a paste of the invention, such paste being contained in the dispenser. The dispenser can be a hand-held tube having an aperture at one end, the tube being of flexible material, such as a resilient plastic, so as to permit controlled issuance of the paste from the tube by squeezing of the tube.

The aperture of the dispenser can have a diameter of between about ⅛" and about ½", more likely about ¼".

The dispenser can be a syringe. The syringe can be a disposable plastic syringe.

In another aspect, the invention is a kit for preparing a medicinal paste. The kit includes a packet of analgesic and a packet of microfibrillar collagen. Preferably, the analgesic and the collagen are provided in pre-determined amounts which can be mixed with a pre-determined amount of a liquid to obtain a paste of suitable consistency for use in a medical procedure such as a surgical operation.

A paste of suitable consistency is one which will flow into all areas desired to be exposed to paste components, but at the same time is viscous enough to resist substantial migration from the treated area over the time period for which pain relief is sought.

The liquid might simply be provided by the analgesic or might be included with the analgesic. If there are other components, such as amino caproic acid and/or an anti-inflammatory, these can be included as part of the kit, and again it would be preferred to have them in pre-determined amounts suitable for use in a surgical operation. One or more of the components might be premixed.

The kit can also include a container with a mixing well for mixing paste components. The kit can also include a syringe for application which contains a mixing head to facilitate mixing prior to application as well as specialty tips for facilitating application of the paste to the desired locations.

The kit can include a mixing stick for mixing the components in the well of the container.

Preferably, the container and stick are sterile and provided in a sealed package.

The kit can include any or all of the components of a paste of the present invention.

In another aspect, the present invention provides a paste which includes an anaesthetic, such as xylocaine. The anaesthetic might be in place of the analgesic, or it might be in addition to the analgesic. Such a paste, in other respects would be similar to that of the analgesic paste of the present invention.

BRIEF DESCRIPTION OF THE DRAWINGS

A description of preferred embodiments is given below, reference being had to the attached drawings.

DETAILED DESCRIPTION OF PREFERRED EMBODIMENTS

In one particular aspect, the present invention involves performing a lumbar discectomy or laminectomy on a human patient, a discectomy being described here. Following removal of a ruptured disc and decompression of the nerve root, including foraminotomy, an analgesic paste of the present invention is applied to the exposed dura and nerve root and disc interspace.

Prior to application of the paste, the operation is carried out in a known manner. For example, general anesthesia is administered to the patient. Twenty milliliters of 0.5% Marcaine® is administered subcutaneously just before the incision is made, to reduce stress (catecholamine, etc.) response to the surgical incision. An intraoperative roentgenogram is taken to confirm the lumbar interspace. A single level microdiscectomy incision for a ruptured lumbar disc, generally not exceeding one inch in length, is made. An additional inch is added for each additional lumbar level. Microneurosurgical techniques are employed.

Figure 1:
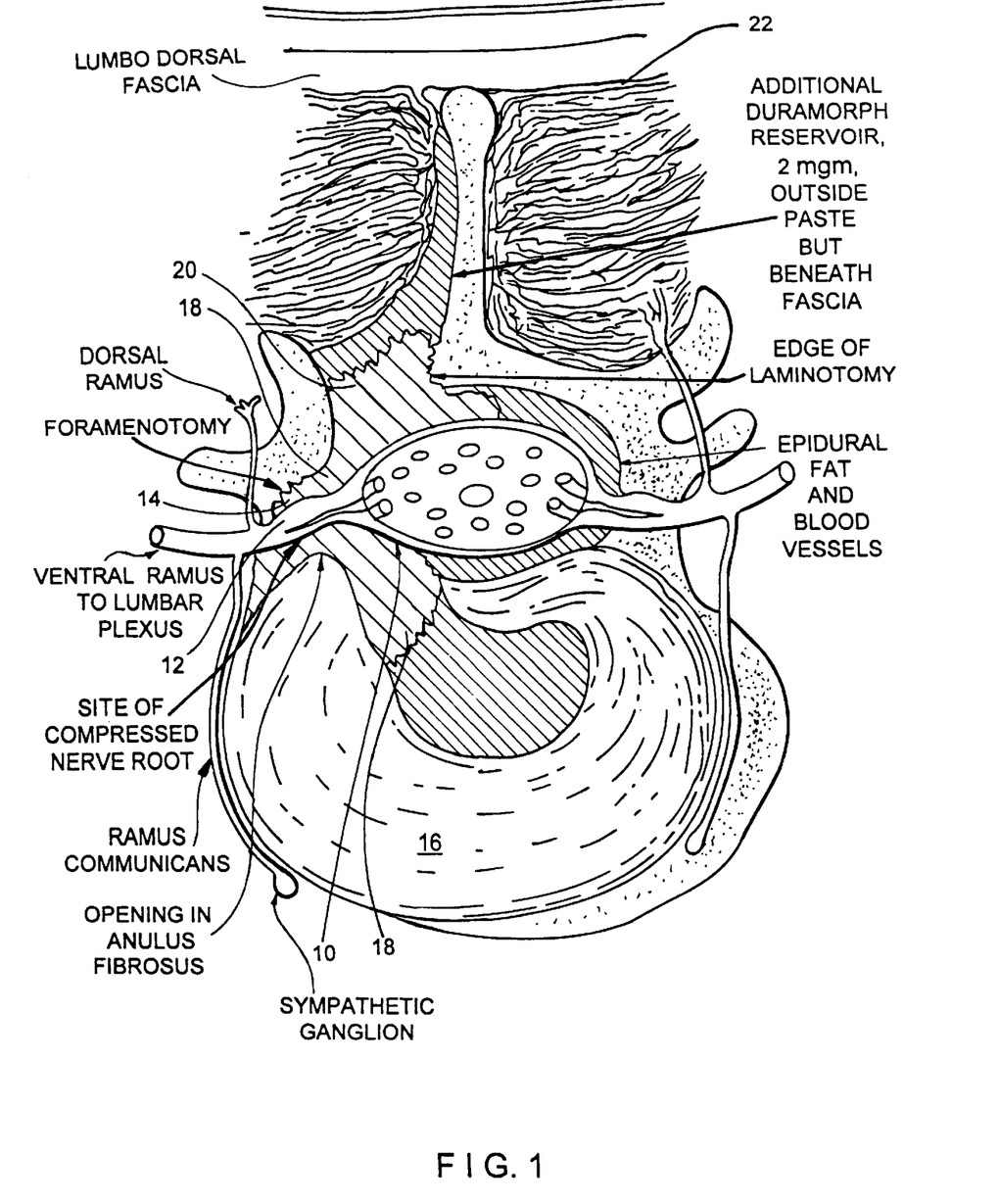
FIG. 1 is a cross sectional view of the lumbar area of a spine after application of analgesic paste of the present invention.

The ruptured disc is removed to decompress the nerve root, possibly including foraminotomy. A paste is prepared, as described below, and applied to the exposed dura and nerve root and disc interspace. No catheters are placed in the epidural space. With reference to the accompanying figure, the paste is generously applied to the exposed dura 10, including the emerging nerve root 12 at the foramen 14. The thick paste is fluid enough to pass beneath the nerve root, anterior to the dural tube, down to the annulus 16. Paste 18 is applied so as to enter the opening 20 in the annulus through which the ruptured disc has been removed. However, the paste is not so fluid as to permit its rapid entry and escape into blood vessels and lymphatics of the general epidural space. The preferred paste, described below, meets perfectly well these requirements, although variations in the composition of the paste are possible. Water-tight closure of lumbodorsal fascia is then carried out with continuous suture. A reservoir of additional sterile morphine (Duramorph® (2 to 4 mg, depending on the length of the incision)) is injected outside the paste, but inside the closure of the lumbodorsal fascia. This injection can also test the watertightness of the closure. This liquid reservoir of morphine seeps into the nerve paste with time, possibly reduces muscle spasm and also separates the paste from the fascial closure. Alternatively, it is possible to include the additional morphine as part of the paste composition. Prophylactic antibiotics, for example oxacillin, although may others are known to a skilled person, are administered intravenously, usually prior to the application of the nerve paste and may be mixed into the paste to help prevent post-operative wound infection.

A preferred paste includes one small package (500 mg) of Avitene®, 2 mL (80 mg) Depo-medrol® (Upjohn), 2 mL (500 mg) Amicar® (aminocaproic acid, Lederle), and 2 mL (1 mg) Duramorph®. The paste can be prepared just prior to use, or possibly prepared ahead of time. The paste is prepared by mixing all of the ingredients together until a substantially homogeneous paste is obtained.

Most preferred paste formulations of the invention are the following:

|  | DISECTOMY | | LAMINECTOMY | |
|---|---|---|---|---|
| GROUP 1 (EVERYTHING) | 0.75 g Avitene 3 mg Epimorph 80 mg Depo-medrol 500 mg Amicar | (6 cc) (2 cc) (2 cc) | 1.0 g Avitene 5 mg Epimorph 80 mg Depo-medrol 500 mg Amicar | (10 cc) (2 cc) (2 cc) |
|  | 10 cc | | 14 cc | |
| GROUP 2 (DEPO-MEDROL) | 0.75 mg Avitene 80 mg Depo-medrol 500 mg Amicar normal saline | (2 cc) (2 cc) (6 cc) | 1.0 g Avitene 80 mg Depo-medrol 500 mg Amicar normal saline | (2 cc) (2 cc) (10 cc) |
|  | 10 cc | | 14 cc | |
| GROUP 3 (MORPHINE) | 0.75 mg Avitene 3 mg Epimorph 500 mg Amicar normal saline | (2 cc) (2 cc) (2 cc) | 1.0 g Avitene 5 mg Epimorph 500 mg Amicar normal saline | (10 cc) (2 cc) (2 cc) |
|  | 10 cc | | 14 cc | |

Subjects were monitored after being operated upon as described above. In fifty-four subjects, no instances of respiratory depression were found. Naloxone hydrochloride (0.4 mg intravenously) may be used if the respiratory rate falls below eight per minute. The Trendelenburg position is avoided. Subjects are maintained in a head-elevated position at 30 degrees for one to two days after the operation. Elderly subjects (over 70 years) may be sensitive to small amounts of morphine. None of the fifty-four subjects complained of pruritis. One lumbar infection was encountered. Two subjects developed postoperative urinary retention requiring catheterization. No postoperative narcotics were required in 98% of subjects. Essential ingredients of the paste of the preferred embodiment are an analgesic and microfibrillar collagen. In the case of the preferred embodiment paste, the analgesic is Duramorph®, which is a preservative-free morphine sulfate. Avitene® is a microfibrillar collagen. It is the microfibrillar collagen, in the correct proportion, that provides the paste with the desired consistency. The consistency should be sufficient to prevent the too rapid escape of paste components from the local epidural space at the operative site.

In the preferred embodiment, the analgesic is morphine. It is expected that other analgesics can be administered using the teachings of this invention, i.e., by combination with microfibrillar collagen to form a paste. Examples of the analgesics include fentanyl and demerol.

The consistency of the paste, which is important, is provided by the microfibrillar collagen. The paste of the preferred embodiment has a viscosity which in the judgement of the inventors is slightly less than that of toothpaste. It may well be, for use in operations other than lumbar spinal operations, a paste having more or less consistency would be desirable. Increasing the relative proportion of the microfibrillar collagen in relation to liguid components of the paste would increase the viscosity, i.e., create a thicker paste. Conversely, decreasing the relative proportion of the microfibrillar collagen in relation to liguid components of the paste would decrease the viscosity, i.e., create a more fluid paste, a paste that would flow more readily. In situations were prolonged release of the analgesic is important, it will of course be desirable to have a paste of thick enough consistency that active ingredients, i.e., the analgesic, are not released too guickly. On the other hand, it may be desirable, in order to obtain flow of the paste into particularly small crevices or the like, to have a paste which flows more readily. While a limited amount of experimentation might be necessary to find the optimum proportions of each component of a paste that work well in a given situation, this is well within the skill of a person skilled in the art, given the disclosure of this invention.

The microfibrillar collagen of the preferred embodiment is commercially available under the name of Avitene®, microfibrillar collagen hemostat (mch), distributed by Med-Chem Products, Inc., Subsidiary of C. R. Bard, Inc., of Woburn Mass., and is apparently described in one or more U.S. Pat. Nos. 3,610,473, 4,016,877 and 4,181,664. The specifications of all of these patents are incorporated herein by reference. The material is an absorbable topical hemostatic agent. It is a dry, sterile, fibrous, water insoluble partial hydrochloric acid salt of purified bovine corium collagen. It is prepared in a loose fibrous form and in a compacted "non-woven" web form. The loose fibrous form was used in the preferred embodiments described herein, but the compacted form could also be used. During preparation, swelling of native collagen fibrils is controlled by ethanol to permit non-covalent attachment of hydrochloric acid to amine groups on the collagen molecule and preservation of the essential morphology of native collagen molecules. Dry heat sterilization causes some cross-linking which is evidenced by reduction of hydrating properties, and a decrease of molecular weight which implies some degradation of collagen molecules.

The preferred embodiment, in addition to an analgesic and microfibrillar collagen, includes an anti-inflammatory agent and amino caproic acid. A paste of the invention can include one or the other or both of these components.

The preferred anti-inflammatory agent is methylprednisolone acetate, but another steroidal or non-steroidal anti-inflammatory agent, or combination thereof, might be substituted for methylprednisolone acetate.

Amino caproic acid is known to inhibit reabsorption of blood clots, which would typically be present at an operative site. It is thought that amino caproic may also prolong the life of the microfibrillar collagen within the operative site, i.e., aid in inhibition of breakdown of the microfibrillar collagen.

While the preferred surgical procedure is a lumbar spinal operation such as a discectomy of laminectomy, it is contemplated that an analgesic paste of the present invention can be used to produce pain relief in other surgical procedures. For example, other indications include spinal operations above the lumbar spine, iliac crest donor sites where bone grafts are taken, etc. Care should be taken, for example, at spinal levels above the lumbar spine, because of a potential for transient complications with respect to respiratory depression and paralysis.

A paste containing morphine would likely not be used in a subject with a known sensitivity to morphine. Care should also be taken to avoid intradural exposure to a paste of the present invention.

Further, while the preferred embodiment paste includes the analgesic morphine, it is contemplated that an anesthetic such as xylocaine could be administered by use of a paste created from the anesthetic and microfibrillar collagen.

It is also expected that since most components making up such a paste have a defined shelf life, it will be possible to pre-mix and package such pastes. Another aspect of the invention is thus a pre-mixed paste contained in a dispenser. A dispenser, containing a paste, that could be used to directly apply the paste during an operation would be particularly suitable. Thus a squeeze tube similar to that used with toothpaste and having a head aperture of suitable diameter for issuance of the paste directly to an operative site is within the scope of this invention. A suitable diameter for such an aperture would generally be between $\frac{1}{8}$" and $\frac{1}{2}$", while one closer to $\frac{1}{4}$" is preferable. Alternatively, a syringe, preferably a plastic disposable syringe is a suitable dispenser for pre-mixed paste. In yet another embodiment, components of a paste are provided in separate packets as part of a kit that includes a container with a mixing well for the components and a mixing stick, the components of the kit being provided in a sealed package. The components can thus be prepared and packaged under suitably hygienic conditions and be protected from the external environment until the paste is to be prepared.

The following examples describe the manner and process of making and using the invention and set forth the best mode contemplated by the inventor of carrying out the invention but are not to be construed as limiting the invention.

EXAMPLE 1 a. Patient Population and Sample Size

From January of 1996 until August of 1997, patients undergoing routine elective lumbar decompressive surgery at the Barrow Neurological Institute were recruited into the study. The population was defined as patients undergoing first-time lumbar microdiscectomy or laminectomy. Inclusion and exclusion criteria are detailed in Table I. After enrollment into the study, patients underwent a detailed neurological examination and were administered 3 questionnaires (McGill Pain Questionnaire (MPQ), Aberdeen Back Pain Index (ABPI), and SF-36 General Health Survey). Participants were stratified into two groups based on the magnitude of the planned surgery (discectomy or laminectomy).

Table I: Inclusion and Exclusion Criteria

Inclusion, any patient undergoing lumbar decompressive surgery for degenerative (non-neoplastic, non-infectious) disease where the dura was to be exposed and fusion/instrumentation was not performed.

Exclusion
- known hypersensitivity to morphine or methylprednisolone radiographic evidence of mechanical instability including spondylolisthesis and scoliosis
- CSF leak
- conus injury
- failed back syndrome
- instrumentation
- pregnancy
- primary language other than English
- surgery extending above L1
- unavailable for extended follow-up On the day of surgery patients were randomized into placebo or control groups. All patients received a standard inhalational anesthetic with supplemental oxygen and nitrous oxide. All surgeries were performed by a single surgeon (VKHS) at a single institution. A morphine-based analgesic paste was applied directly to the exposed dura at completion of the decompression, prior to wound closure. The ingredients and technique were identical to those previously described by Needham (Needham, 1996). Briefly morphine, solumedrol, aminocaproic acid, and microfibrillar collagen (Avitene. Davol Inc., Subsidiary of C. R. Bard, Inc., Cranston, R. I.) were combined into a paste form. A further amount of morphine was injected into the epidural space following muscle or fascial closure, the quantity defined by the type of operation (discectomy vs. laminectomy). The placebo mixture lacked both morphine and solumedrol, replaced volume for volume with normal saline. The paste was mixed in a sterile field at the time of surgery by an investigator not involved in patient care or follow-up. The patient, surgeon, and on-site study nurse were blinded and remain so for the duration of follow-up (1 year total). The study was terminated when significance of the primary outcome measures was established (n=30 for each of the two study groups, n=15 for each of the surgical procedures within each study group).

b. Follow-Up

Follow-up continues on all patients for a duration of one year from the time of surgery. We report here on the early (12 week) results.

c. Outcome Measures

Demographic information was collected prospectively on each patient including age, sex, weight, occupation, smoking history, and duration of symptoms. Patients were assessed pre- and post-operatively with both physician-derived and patient-derived outcomes. In addition, hospital-derived outcomes were also recorded.

Physician-derived outcomes included a detailed motor and sensory exam quantified according to a modified ASIA scale. In addition results from bilateral passive straight leg raising tests were recorded. These data were obtained pre-operatively, and on day 1 post-operatively.

Patient-derived outcomes were in the form of three questionnaires, administered in person or by telephone. Three components of the McGill Pain Questionnaire (MPQ) were administered preoperatively, and post-operatively on day 1, week 1, week 3, week 6, and week 12 (PRI(R), NWC, PPI). The Aberdeen Back Pain Index (ABPI) and SF-36 general health questionnaire were given pre-operatively and post-operatively at weeks 3, 6, and 12.

Hospital-derived outcomes were obtained by nursing staff involved in the care of patients during their hospital stay (also blinded to treatment group). Information collected included vital signs (blood pressure, heart rate, respiratory rate) and continuous oxygen saturation monitoring. All parameters were charted every two hours throughout the patient's stay. Quantitative records of analgesics delivered in the recovery room and on the floor were obtained from patient medication records for the duration of hospitalization by the on-site study nurse. In addition she surveyed each patient at regular postoperative intervals documenting postoperative complications such as urinary retention, wound difficulties, pruritis, and symptom recurrence. Following discharge patients reported home analgesic consumption to the on-site study nurse at weeks 1, 3, 6 and 12 based on prescription renewal and remaining pills.

d. Data Analyses

All data was forwarded to the second institution for un-blinding and ongoing analyses. Questionnaires were scored initially by the on-site blinded study nurse, and then rechecked by the off-site nurse. Discrepancies were resolved by the principle investigator according to the published guidelines for each questionnaire. Descriptive statistics were compiled for all primary and secondary outcome measures. Data were checked for normality using the Kolmogorov-Smirnov test with Lilliefors' correction.

Parametric tests of significance were performed by repeated measures analysis of variance or paired t-test. Non-parametric data (resistant to transformation) were analyzed by the Mann-Whitney Rank Sum test. Probability levels for significance were defined as a p value $\leq 0.05$. For these analyses prepared Oct. 8, 1997, data points for two patients at 6 weeks and three patients at 12 weeks were not yet available.

Results

Sixty patients were successfully randomized to each of the treatment arms (placebo vs. paste), stratified for operative procedure (15 laminectomy and 15 discectomy in each arm). All patients remained in the study throughout the duration of their follow-up. All patients were available for three month assessment.

a. Comparability Between Groups

Both groups of patients were similar in respect to demographic characteristics. There were 11 females and 19 males in the placebo group, while there were 12 females and 18 males in the paste group. The average age of patients in the placebo group was 50 years (±3 std. err.) whereas the average age in the paste group was 53 years (±3) (t-0.752; d.f 58; p=0.46). The average patient weight for the placebo group was 79 kg. (±4) and 86 (±5) for the paste group (t-1.181; d.f 40; p=0.25). There were no statistical differences between the two groups in comparing employment status, marital situation, smoking history, or incidence of co-morbidity (p>0.05, $\chi^2$). Pre-operative physical examinations revealed similar motor and sensory scores for placebo and paste patients (motor=49±0.24 placebo, 48±0.57 paste; sensory=78±0.71 placebo, 78 (±0.82) paste). General health perception as measured by the SF-36 questionnaire was similar among groups (t 0.355; d.f 58; p=0.72). Both groups experienced about the same amount of pain pre-operatively as indexed by all three facets of the MPQ and the ABP (p>0.05, ANOVA).

b. Complications

There were no intra-operative complications recognized at the time of surgery. One patient in the paste group developed a CSF leak recognized post-operatively. This was treated uneventfully with an extra skin suture. Eight patients from the placebo group required intermittent catheterization in the immediate post-operative state for temporary urinary retention. Six patients were similarly afflicted in the paste group. All patients regained normal bladder function within 24 hours of the anesthetic.

One patient from the paste group developed a superficial wound infection treated successfully with local measures at home. There were no reported instances of itching or rash in either group.

c. Course in Hospital

All study subjects were monitored closely for alterations in oxygen saturation, respiratory rate, and blood pressure during their hospital stay. Minimum oxygen saturation was comparable between placebo (95% ±1) and paste (93% ±3) groups (p=0.74, Mann-Whitney Rank Sum). The minimum respiratory rate observed was also similar for placebo (14 ±1) and paste (14 ±1) patients (p=0.63, Mann-Whitney Rank Sum). There was no significant difference in mean maximum systolic (142 mm Hg both groups) or diastolic (72 mm Hg placebo, 74 mm Hg paste) blood pressure between patients. Similarly minimum systolic blood pressure was not notably different (109 mm Hg vs. 111 mm Hg, placebo vs. paste). However the placebo patients tended to have a lower minimum diastolic blood pressure (60 mm Hg ±2) compared to paste patients (68 mm Hg ±2) (t-2.437; d.f=58; p=0.018).

Length of hospital stay was similar between the two groups (mean=2 days both groups, 55 cumulative days for all patients in the placebo group, 52 cumulative days for all patients in the paste group).

d. Primary Outcome Measures

Figure 2:
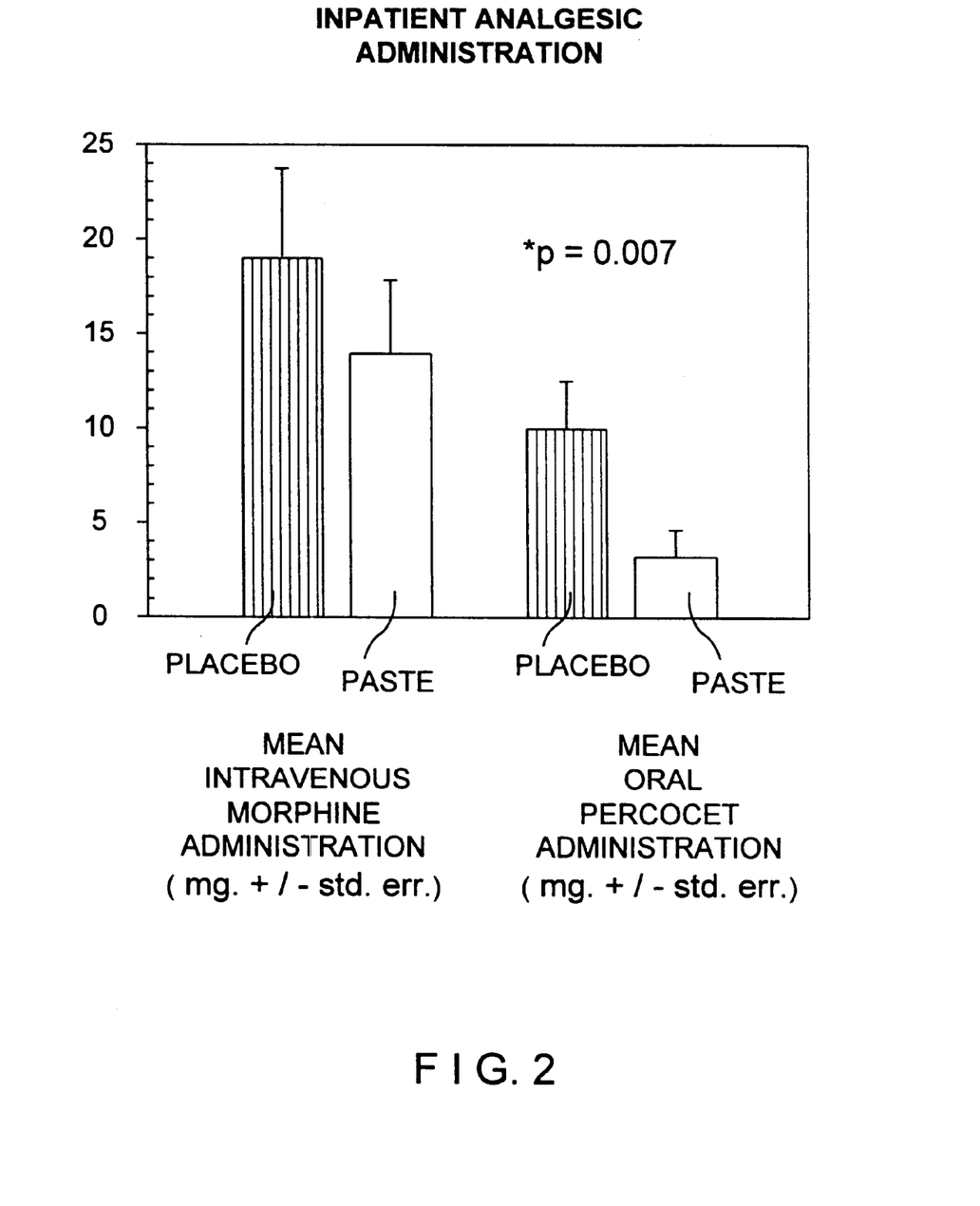
FIG. 2 is a graphical representation of inpatient analgesic administration in patients given paste compared to those treated without.

Those subjects receiving active paste consumed less narcotic analgesics while in hospital and while at home throughout the 3 months of follow-up. The mean in-patient cumulative morphine dose was 19 mg. for placebo patients and 14 mg. for paste patients. This did not reach statistical significance (p=0.16, Mann-Whitney Rank Sum). More striking was the difference in oral analgesic consumption (FIG. 2). Placebo patients took over three times as many percocet tablets during their hospital stay compared to paste patients (p=0.007, Mann-Whitney Rank Sum).

Figure 3:
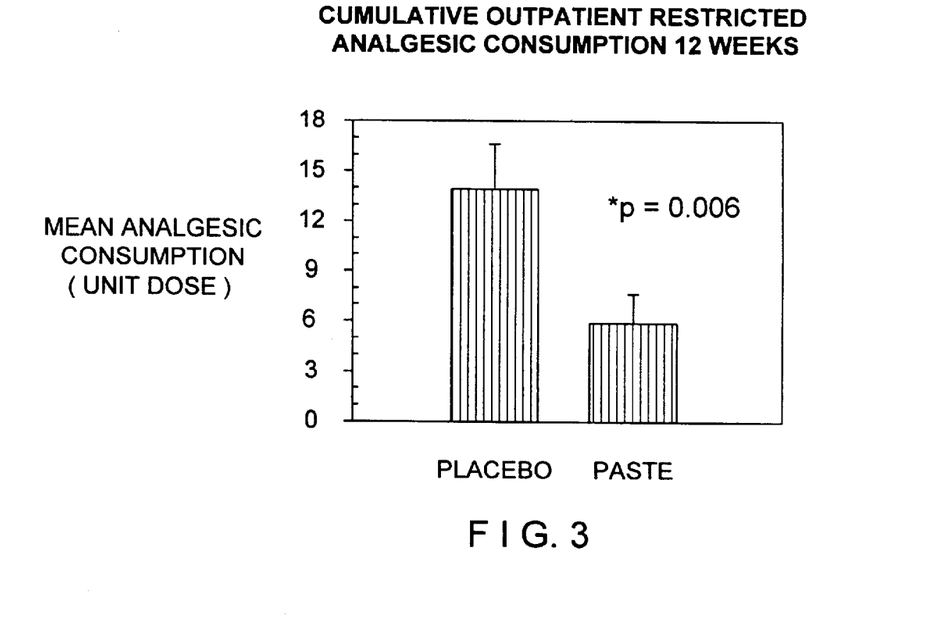
FIG. 3; patient reported prescription analgesic consumption was significantly less in those patients receiving active paste compared to controls throughout the three months of follow-up.
Figure 4:
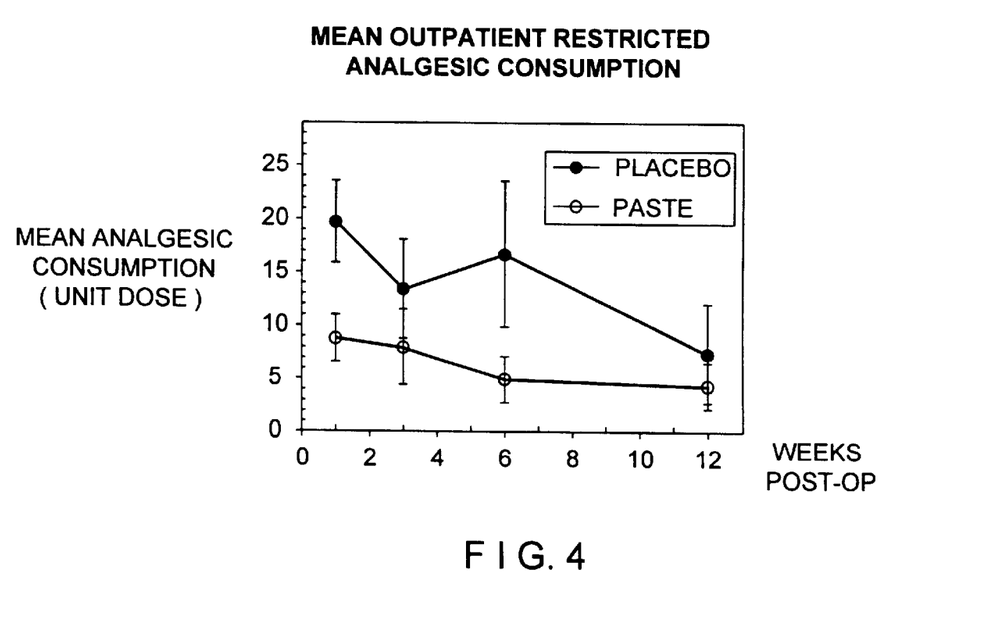
FIG. 4; mean prescription analgesic consumption as a function of time post-operatively, only at 12 weeks do placebo patients approach the lower analgesic levels of the paste patients.

This trend continued into the postoperative convalescence at home. Patients who received active paste reported taking less than half of the amount of controlled analgesics compared to placebo patients (p=0.006. Mann-Whitney Rank Sum). Post-hoc analysis demonstrated prescription analgesic consumption in placebo patients to be higher than those receiving paste through weeks three and six, dropping to comparable levels by week 12 (FIGS. 3 and 4).

Figure 5A:
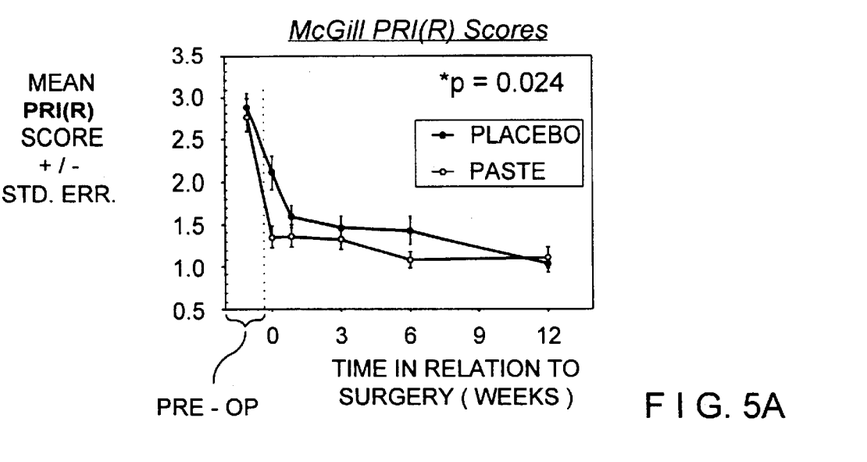
FIGS. 5A–5C; post operative pain levels indexed by three arms of the McGill Pain Questionnaire.
Figure 5B:
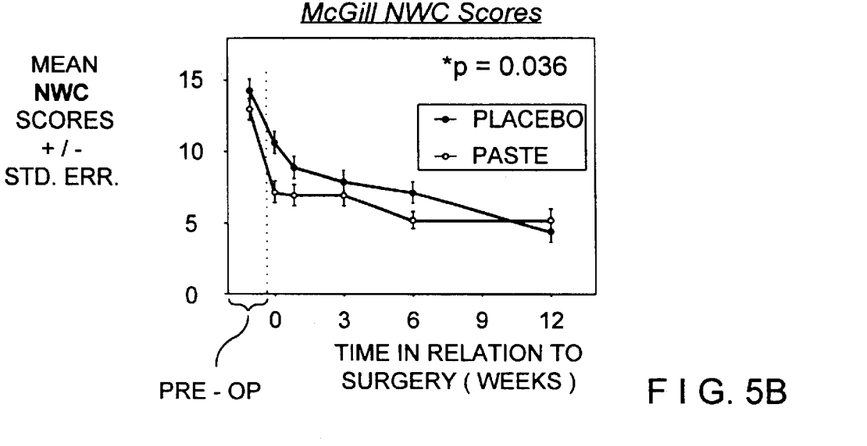
Figure 5C:
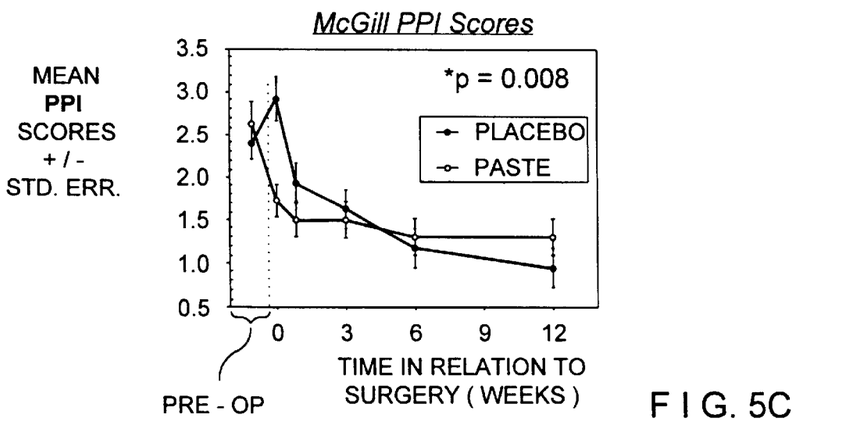

Patient perceived discomfort as indexed by the McGill Pain Questionnaire was significantly lower through the post-operative period in patients receiving active paste compared to controls. The PRI(R) and NWC indices were markedly less on day 1 post-op in actively treated patients compared to controls. These differences lessened but nonetheless persisted through weeks three and six becoming comparatively similar at week 12 (FIG. 5). The PPI (a more volatile index) indicated lower pain levels in paste patients post-operatively and at week three compared to controls, becoming similar at week 6. Surgery was clearly effective in reducing pain levels in patients from both groups.

Figure 6:
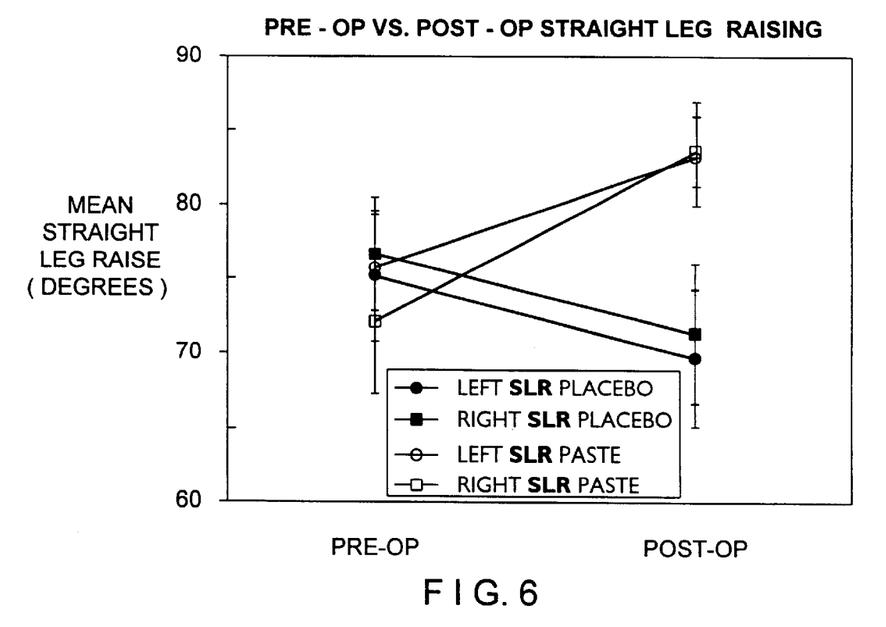
FIG. 6; change in straight leg raise (angle) after surgery. Ability to have the leg passively raised in extension at the knee improved in those patients receiving paste but decreased in controls.

Post-operative neurological exammiation revealed similar motor (49 ±0.2 placebo, 50 ±0-1 paste) and sensory scores (79 ±0.3 placebo, 78 ±0.8 paste) between groups. Interestingly, the mean left and right straight leg raise results improved from 76° (±4) to 83° (±4) and 72° (±5) to 84° (±2) respectively in the paste group. However, in the placebo group mean left and right straight leg raise scores decreased from 75° (±4) to 70° (±5) and 77° (±4) to 71° (±5) respectively on day one post-op (FIG. 6). Although compelling, these differences did not achieve statistical significance.

Figure 7:
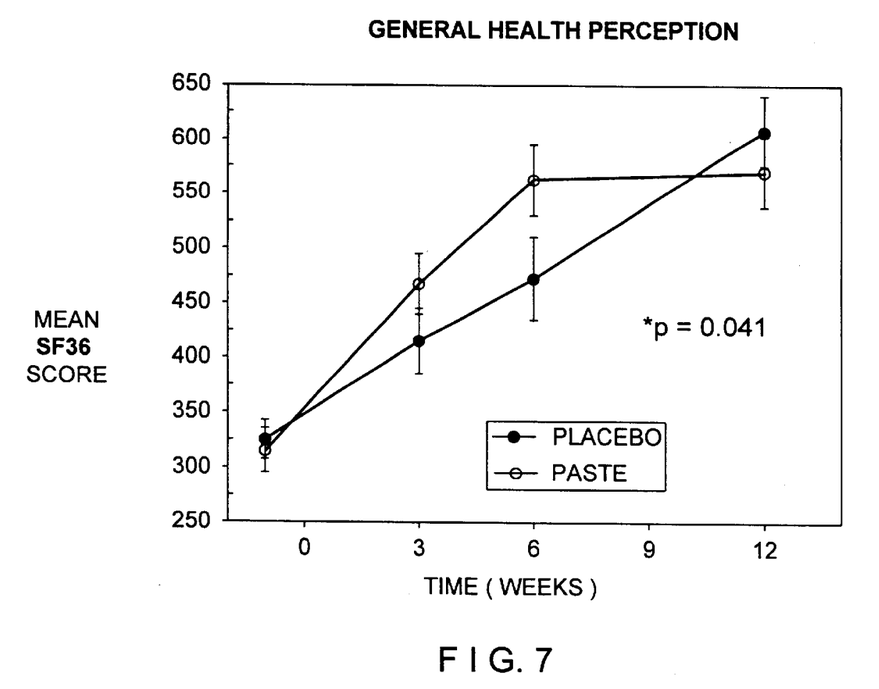
FIG. 7 graphically shows perception of general health observed in patients.

General health perception was assessed by the SF-36 questionnaire. Somewhat unexpectedly, we observed an improvement in overall health perception post-operatively in patients receiving paste compared to those receiving placebo. A statistically significant interaction was found between group and time over the 3 month period encompassing our follow-up (F=2.976; d.f 3,234; p=0.041). General health perception was better in paste patients 3 and 6 weeks post-operatively. At 12 weeks both groups had achieved similar general health profiles. Sub-section analyses demonstrated trends towards improved scores in physical functioning, role functioning, bodily pain, vitality, emotional health, and mental health for paste patients compared to placebo patients. Although ABP scores tended to be better in patients receiving paste 3 and 6 weeks post-operatively, this effect was not statistically significant, (see FIG. 7).

Conclusions

The results of this study support several conclusions. In addition to the statistical significance achieved in many of the outcome measures, a high degree of internal consistency over time between analgesic consumption, patient reported pain, and general health profiles through the 12 week follow-up lends further credibility to these conclusions.

Application of this morphine-based analgesic paste in lumbar decompressive surgery has proven safe in this group of patients. We encountered no complications or complaints attributable to use of this compound. Of note is the absence of respiratory depression and itching in this series.

Use of the paste not only reduces the need for inpatient and outpatient analgesic administration (by a factor of 2–3 times), but also provides significantly better pain control compared to the current gold standard of medical practice. In addition patient perception of general health status is also improved.

The beneficial effects of the analgesic paste compared to current standard of care, are present within 24 hours of application and persist for approximately 6 weeks from the time of surgery. Long-term pain control of this magnitude with a single application has not previously been reported.

These observations suggest that use of this morphine-based paste be considered as a new standard of care in patients undergoing lumbar decompressive surgery.

EXAMPLE 2

Four level lumbar laminectomies were performed on 20 female white New Zealand rabbits which were randomized into one of four groups after surgery. The first group of 5 animals consisted of the epidural control (EC) group who underwent the standard laminectomy. The second group of five animals was the epidural morphine (EM) paste group who underwent the standard laminectomy with the epidural application of one-half of a standard dosage of MNP. The third group of five animals served as the intradural control (IC) group who underwent standard laminectomy and opening of the dura. The dura was left open and the subcutaneous tissues and skin were closed in standard fashion. The fourth group was the intradural morphine (IM) paste group who underwent standard laminectomy with opening of the dura with intradural application of one-half of a standard dosage of MNP directly onto the spinal cord. The spines were removed, fixed in 10% formaldehyde and subjected to CT scanning in the sagittal and axial planes through the thickest area of the laminectomy site. The CT scans were then reviewed by 2 blinded neuroradiologists. Specimens were then examined grossly before being decalcified, sectioned in the sagittal and transverse planes and stained with hematoxylin and eosin. The slides were then reviewed by a blinded neuro-pathologist.

Results

Four animals had to be sacrificed and replaced during this experiment. Two suffered neurological injury during the initial surgery and were rendered paraplegic. The animals exhibited behavior consistent with a dyseathetic pain syndrome and were observed to be chewing on their hind limbs. After a discussion with the consultant veterinarian, it was decided to sacrifice these animals. Two other animals were sacrificed after developing wound infections within one week of surgery. One animal was in the EC group and the other was in the EM group. Review of the surgical procedure revealed a break in aseptic surgical technique. Once this was identified, there were no further wound infections.

There were no instances of late neurologic deficit, infection or other complications noted prior to the sacrifice of all animals that survived greater than one week postoperatively.

Review of CT scans through the affected spines of the EC group revealed no soft tissue mass or thickening. What was prominent in this group, however, was severe and extensive soft tissue ossification. This was so severe in 4 of 5 specimens that the laminectomized levels had been completely overgrown by new bone. The was contrasted with the EM group which also showed no soft tissue mass or thickening. There was no significant soft tissue ossification in 4 out of 5 specimens.

CT scans through the affected spines of the IC group showed no soft tissue mass or thickening. There was no significant soft tissue ossification in 4 out of 5 specimens. The IM group also showed no soft tissue mass or thickening. There was mild soft tissue ossification in 3 out of 5 specimens which did not extend beyond the laminectomy level. No other significant or consistent abnormalities were noted.

Histologic evaluation of the EC group revealed new bone formation at the laminectomy site with extensive fibroplasia. The dura was intact without injury to the underlying spinal cord. No significant inflammation was seen.

Evaluation of the EM group also revealed new bone formation at the laminectomy site with extensive fibroplasia. The dura and underlying spinal cord were unremarkable in this group. What was seen, however, was chronic inflammation in the overlying fat and muscle with foreign body giant cells as well as rare neutrophils. Foamy macropnages were also present. Detailed examination of these foci of inflammation were possibly thought to be consistent with suture granulomas as they were punctate in nature and evenly spaced throughout the deep muscle and fat layers.

Comparison of the two epidural groups was significant for the inflammatory cells seen in the fat and muscle of the EM group. No other significant differences were seen when comparing these two groups. There was no injury to the underlying dura or spinal cord in either group.

The IC group also showed new bone formation at the laminectomy site with extensive fibroplasia. There was mild chronic inflammatory cells in the fibrous tissues nearest the cord, however, the cord itself was unremarkable.

The IM group showed now bone formation at the laminectomy site as well as extensive fibroplasia. There was a mild aggregation of inflammatory cells seen in the tissue nearest the cord . The spinal cord itself showed no evidence of injury or chronic inflammatory changes.

Comparison of the two intramural groups show them to be histologically indistinguishable. Both have mild inflammatory infiltrates without injury or inflammation of the underlying exposed spinal cord.

This is the first laboratory study evaluating the usage of a morphine containing nerve paste In the epidural and subdural spaces. The constituent ingredients, with the exception of epsilon aminocaproic acid have all been used extensively in the epidural space and are approved for such usage by the FDA.

Microfibrillar collagen has been used extensively as a hemostatic agent with excellent results. It is bioassimable without producing a significant foreign body response. It is generally absorbed by macrophages within 3 to 7 weeks and demonstrates minimal, if any, increased antigenicity. Most studies also show that microfibrillar collagen doe not increase the risk of infection.

Epidural steroids are commonplace in the treatment of low back and neck pain. The effectiveness of epidural steroids, while debatable by some, has been validated by numerous prospective, controlled studies. The local effect of epidural steroids does not seem to be a significant risk to neural tissue.

Complications are uncommon but include Cushing's syndrome secondary to excess glucocorticoid administration. Other potential complications are infrequent and include meningitis, subcutaneous abscess, and CSF-cutaneous fistula. The aforementioned complications are uncommon and are almost exclusively associated with the percutaneous injection of epidural steroids.

Epidural narcotics such as morphine have been used extensively and their safety and efficacy validated in numerous studies. Side effects include respiratory depression, pruritus, nausea and vomiting, and urinary retention. Hydrophilic opiods such as morphine are readily metabolized and there have been no reports of significant long term adverse effects from their usage in the acute postoperative state. Complications related to epidurally administered opiods are mostly related to infusion via a catheter and include epidural hematoma, epidural abscess and overclosage.

Epsilon aminocaproic acid (Amicarg) is a water soluble 6-aminohexanoic acid which acts as an inhibitor of fibrinolysis. Its actions are exerted principally by inhibition of plasminogen activators and also to a smaller degree through antiplasmin activity. It is principally used to enhance hemostasis when fibrinolysis contributes to bleeding as in patients with aneurysmal subarachnold hemorrhage. As part of the MNP, aminocaproic acid theoretically acts as a local inhibitor of fibrinolysis. This may allow the normal postoperative coagulum and MNP to remain in active concentrations longer before being redistributed to the systemic circulation. The dose of epsilon aminocaproic acid used in MNP is very small compared systemic therapeutic closes. Side effects of this medication are minimal and are almost always associated with higher dosages.

In this study the long term effects of post-laminectomy application of MNP were studied. CT examinations of the EC and EM groups showed no significant soft tissue mass or thickening consistent with excessive scarring. Curiously, the EC group showed a predilection (4/5 rabbits) towards formation of soft tissue ossification overlying the laminectomy whereas the EM did not (1/5). This may be due to the presence of the MNP in the EM group which prevented new bone formation in the first few months as the compounds were being resorbed. There were no detectable abnormalities in the EM group, only a tendency to have less ossification of the soft tissues.

Evaluation of the intradural group showed no significant soft tissue mass or thickening and a variable ossification pattern. There was no compression of the spinal cord in any specimen.

Histological analysis showed new bone formation and fibrosis in all specimens. Several specimens had evidence of inflammatory response, however, this may have been due to a reaction to suture material. The IM group did show the formation of a mild inflammatory aggregate near the spinal cord, however, there was no evidence clinically or histologically of neural damage in any group. Late complications such as significant scarring around neural tissue or damage to neural elements was not seen.

What is claimed is:

1. A medicinal paste for use in a surgical procedure performed on a mammal, including a human, to reduce pain, which comprises;

an analgesic; and a microfibrillar collagen.

2. The paste of claim 1 wherein the analgesic is selected from the group consisting of morphine, fentanyl, demerol and a combination thereof.

3. The paste of claim 2 wherein the analgesic selected is morphine.

4. The paste of claim 1 which further comprises an effective amount for anti-inflammatory activity of an anti-inflammatory agent.

5. The paste of claim 4 wherein the anti-inflammatory agent is a steroidal compound.

6. The paste of claim 5 wherein the agent is methylprednisolone acetate.

7. The paste of claim 5 which further comprises a portion of amino caproic acid.

8. The paste of claim 1 wherein the proportion of collagen is in the range of 100 to 1000 mg and the proportion of analgesic is in the range of from 10 to 500 mg.

9. A method of performing surgery on a mammal, including a human, which comprises;

making an incision which exposes nerves; and applying an effective amount of a paste of claim 1 to at least some of the exposed nerves so as to provide pain relief to the mammal.

10. The method of claim 9 which further comprises closing the incision so as to secure the paste in place to provide prolonged analgesic relief.

11. The method of claim 10 wherein the surgical procedure is a disectomy or a laminectomy.

12. The method of claim 10 wherein the procedure is a treatment for lumbar stenosis.

* * * * *